(12) United States Patent
Considine et al.

(10) Patent No.: US 7,126,025 B2
(45) Date of Patent: Oct. 24, 2006

(54) SYNTHESIS OF 4-(AMINO)-2-BUTENOYL CHLORIDES AND THEIR USE IN THE PREPARATION OF 3-CYANO QUINOLINES

(75) Inventors: John Leo Considine, Bridgewater, NJ (US); Sylvain Daigneault, Laval (CA); Warren Chew, Montreal (CA); Silvio Iera, Montreal (CA); Scott Mason Duncan, Madison, WI (US); Jianxin Ren, Nanuet, NY (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/758,187

(22) Filed: Jan. 15, 2004

(65) Prior Publication Data

US 2004/0162442 A1 Aug. 19, 2004

Related U.S. Application Data

(60) Provisional application No. 60/441,470, filed on Jan. 21, 2003.

(51) Int. Cl.
C07C 51/58 (2006.01)
C07D 215/00 (2006.01)

(52) U.S. Cl. .................................. 562/868; 546/153

(58) Field of Classification Search ............... 562/868; 564/142, 143
See application file for complete search history.

(56) References Cited

U.S. PATENT DOCUMENTS

| | | | |
|---|---|---|---|
| 4,193,983 A | 3/1980 | Ullman et al. | |
| 4,194,050 A | 3/1980 | Hazama | |
| 4,195,021 A | 3/1980 | Herron et al. | |
| 4,478,959 A | 10/1984 | Bechara et al. | |
| 4,565,843 A | 1/1986 | Dünwald | |
| 4,576,759 A | 3/1986 | Viehe et al. | |
| 4,664,825 A | 5/1987 | Walsh | |
| 6,002,008 A | 12/1999 | Wissner et al. | |
| 6,617,333 B1 * | 9/2003 | Rabindran et al. | 514/291 |

FOREIGN PATENT DOCUMENTS

| | | |
|---|---|---|
| EP | 0 448 078 A | 9/1991 |
| WO | WO 98/43960 | 10/1998 |
| WO | WO 03/020266 | 3/2003 |
| WO | WO 2004/066919 A | 8/2004 |

OTHER PUBLICATIONS

Wissner, Allan; et al; Synthesis and Structure—Activity Relationships of 6,7-Disubstituted 4-Anilinoquinoline-3-carbonitriles. The Design of an Orally Active, Irreversible Inhibitor of the Tyrosine Kinase Activity of the Epidermal Growth Factor Receptor (EGFR) and the Human Epidermal Growth Factor Receptor-2 (HER-2); J. Med. Chem., 46:49-63, 2003.

Balenovic, K.; Contribution to the Knowledge of Gamma-Aminocrotonic Acid; J. Org. Chem. 19:1589-1593, 1954.

Traxler P., "Tyrosine kinase inhibitors in cancer treatment (Part II)", Expert Opinion on Therapeutic Patents, Dec. 1998, vol. 8, No. 12, pp. 1599-1625.

Bridges A.J., "Current progress towards the development of tyrosine kinase inhibitors as anticancer agents", Emerging Drugs, 1998, 3:279-292.

Mattsson et al., "Current Concepts in Restenosis Following Balloon Angioplasty", Trends Cardiovasc. Med., Sep. 1995, 5:200-204.

Shaw et al., "Pharmacological inhibition of restenosis: learning from experience", Trends Pharmacol. Sci., Dec. 1995, 16:401-404.

Raines et al., "Multiple growth factors are associated with lesions of atherosclerosis: specificity or redundancy?", Bioessays, Apr. 1996, 18(4):271-282.

Shawver et al., "Receptor tyrosine kinases as targets for inhibition of angiogenesis", Drug Discovery Today, Feb. 1997, 2(2): 50-63.

Folkman, "Angiogenesis in cancer, vascular, rheumatoid and other disease", Nat Med., Jan. 1995, 1(1):27-31.

Boyce et al., "Requirement of pp60c-src expression for osteoclasts to form ruffled borders and resorb bone in mice", J Clin Invest., Oct. 1992, 90(4):1622-1627.

Marszak I. et al., "Recherches sur les Aminoacides et Leurs Derives. I.-sur la Synthese des Aminoacides a Partir des Amines Tertiaires a Fonction Acetylenique Vrai Amino Acids and Their Derivatives. I. The Synthesis of Amino Acids From Tertiary Amnes Having a True Acetyl", Bulletin de la Societe Chimique de France, Societe Francaise de Chimie, 1959, pp. 182-185.

European Search Report for European Patent Application No. 05019642.7 (Mar. 30, 2006).

* cited by examiner

Primary Examiner—Brian J. Davis
(74) Attorney, Agent, or Firm—Howson & Howson; Joseph M. Mazzarese

(57) ABSTRACT

This invention provides a compound of Formula (I):

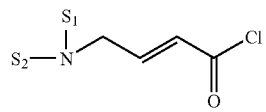

wherein $S_1$ and $S_2$ are each independently, hydrogen, alkyl, alkenyl, alkynyl, aralkyl, substituted or unsubstituted aryl, and $S_1$ and $S_2$ together with the nitrogen to which they are attached form a nitrogen containing heteroaryl and a pharmaceutically acceptable salt thereof; a method of preparing the compound of Formula (I), and use of the compound of Formula (I) in the preparation of 3-cyano quinolines.

12 Claims, No Drawings

SYNTHESIS OF 4-(AMINO)-2-BUTENOYL CHLORIDES AND THEIR USE IN THE PREPARATION OF 3-CYANO QUINOLINES

This application claims priority from now abandoned Provisional Application Ser. No. 60/441,470, filed Jan. 21, 2003, the entire disclosure of which is hereby incorporated by reference.

BACKGROUND OF THE INVENTION

Protein kinases are enzymes that catalyze the transfer of a phosphate group from ATP to an amino acid residue, such as tyrosine, serine, threonine, or histidine on a protein. Regulation of these protein kinases is essential for the control of a wide variety of cellular events including proliferation and migration. Specific protein kinases have been implicated in adverse conditions including cancer [Traxler, P. M., *Exp. Opin. Ther. Patents*, 8, 1599 (1998); Bridges, A. J., *Emerging Drugs*, 3, 279 (1998)], restenosis [Mattsson, E., *Trends Cardiovas. Med.* 5, 200 (1995); Shaw, *Trends Pharmacol. Sci.* 16, 401 (1995)], atherosclerosis [Raines, E. W., *Bioessays*, 18, 271 (1996)], angiogenesis [Shawver, L. K., *Drug Discovery Today*, 2, 50 (1997); Folkman, J., *Nature Medicine*, 1, 27 (1995)] and osteoporosis [Boyce, *J. Clin. Invest.*, 90, 1622 (1992)].

Described in WO9843960 (U.S. Pat. No. 6,002,008) is the laboratory scale synthesis of 3-cyanoquinoline derivatives which include 4-dimethylamino-but-2-enoic acid [4-(3-chloro-4-fluoro-phenylamino)-3-cyano-7-ethoxy-quinolin-6-yl]-amide, inhibitors of protein tyrosine kinases used in the treatment of cancer.

BRIEF SUMMARY OF THE INVENTION

This invention relates to certain novel 4-amino-2-butenoyl chlorides, processes for their preparation and their use as intermediates in the synthesis of pharmaceutically active protein kinase inhibitors.

The present invention provides processes suitable for the preparation of these compounds on a large scale. Furthermore, the invention provides intermediates useful in such processes.

This invention provides a synthetic procedure amenable to large-scale pilot plant work for the manufacture of compounds of Formula (II):

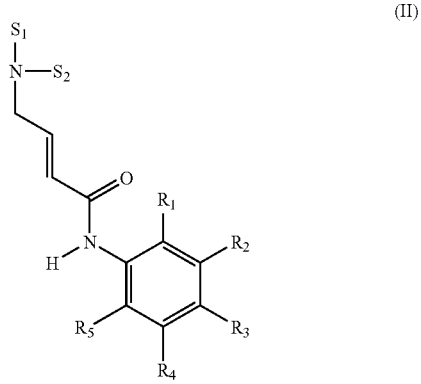

comprising cooling a suspension of pharmaceutically acceptable salt of the compound of Formula (I) adding a chlorinating agent to the suspension; warming and stirring the suspension until the chlorinating agent is completely consumed; cooling the suspension; adding an aniline dropwise to the suspension until the concentration of the aniline is less than about 5%; adding an aqueous base to the suspension to obtain a precipitate; filtering and washing and drying the precipitate to yield the compound of Formula (II).

In an embodiment of this invention the compound of Formula (II) comprises 4-dimethylamino-but-2-enoic acid [4-(3-chloro-4-fluoro-phenylamino)-3-cyano-7-ethoxy-quinolin-6-yl]-amide. In another embodiment of the invention the compound of Formula (II) comprises 6-(4-N,N-dimethylaminocrotonyl)amido-4-(4-(2-pyridylmethoxy)-3-chloro)amino-3-cyano-7-ethoxyquinoline. In yet another embodiment of the invention the compound of Formula (II) comprises 6-(4-N,N-dimethylaminocrotonyl)amido-4-(4-benzyloxy-3-chloro)amino-3-cyano-7-ethoxyquinoline.

This invention also provides a process for the preparation of the compound of Formula (I) comprising reacting a 4-bromocrotonate with $S_1,S_2$—N—R, wherein R is H, trialkylsilyl, alkali metal and $S_1$, $S_2$ are each independently, hydrogen, alkyl, alkenyl, alkynyl, aralkyl, substituted or unsubstituted aryl, cycloalkyl, cycloalkenyl, or $S_1$, and $S_2$ together with the nitrogen to which they are attached form a nitrogen containing heteroaryl; or a pharmaceutically acceptable salt thereof, to obtain 4-$S_1,S_2$-aminocrotonate; hydrolyzing 4-$S_1,S_2$-aminocrotonate in the presence of a base; adding HCl to the compound; and chlorinating the compound with a chlorinating agent to obtain the compound of Formula (I).

In one embodiment of the invention the $S_1$ and $S_2$ are $CH_3$ and the process for the preparation of the compound comprises reacting but-2-enoic acid with chlorotrimethylsilane to obtain trimethylsilylcrotonate; brominating trimethylsilylcrotonate with a brominating agent to obtain trimethylsilyl-4-bromocrotonate; reacting trimethylsilyl-4-bromocrotonate with dimethylamine to obtain 4-dimethylaminocrotonic acid; chlorinating of 4-dimethylaminocrotonic acid hydrochloride with a chlorinating agent to obtain (E)-4-(Dimethylamino)-2-butenoyl chloride.

This invention also provides a compound of Formula (I):

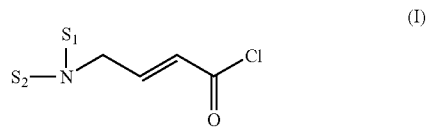

wherein $S_1$ and $S_2$ are each independently, hydrogen, cycloalkyl, cycloalkenyl, alkyl, alkenyl, alkynyl, aralkyl, substituted or unsubstituted aryl or heteroaryl, or $S_1$ and $S_2$ together with the nitrogen to which they are attached form a nitrogen containing heteroaryl or cycloheteroalkyl; or an acid addition salt thereof.

In one embodiment the compound of Formula (I) is (E)-4-(Dimethylamino)-2-butenoyl chloride.

In another embodiment this invention provides a process for the preparation of a compound of the invention comprising:

(a) reacting a 4-bromocrotonate with $S_1,S_2$—N—R wherein R is H, trialkylsilyl or alkali metal and $S_1$ and $S_2$ are as defined above or an acid addition salt thereof to obtain the corresponding 4-$S_1,S_2$-aminocrotonate;

(b) hydrolyzing 4-$S_1,S_2$-aminocrotonate of step (a) in the presence of a base; and isolating as a corresponding hydrochloride salt; and (c) chlorinating the compound of step (b) with a chlorinating agent to obtain the compound of Formula (I).

In one embodiment of the invention $S_1$ and $S_2$ are $CH_3$ or an acid addition salt thereof and the process for the preparation of the compound comprises:
(a) reacting but-2-enoic acid with chlorotrimethylsilane to obtain trimethylsilylcrotonate;
(b) brominating trimethylsilylcrotonate of step (a) with a brominating agent to obtain trimethylsilyl-4-bromocrotonate;
(c) reacting trimethylsilyl-4-bromocrotonate of step (b) or methyl or ethyl 4-bromocrotonate with dimethylamine to obtain 4-dimethylaminocrotonic acid; and
(d) isolating the compound of step (c) as a hydrochloride salt and chlorinating with a chlorinating agent to obtain the compound of of the invention wherein 1 wherein $S_1$ and $S_2$ are $CH_3$.

In another embodiment the invention provides a process for the preparation of a compound of Formula (II):

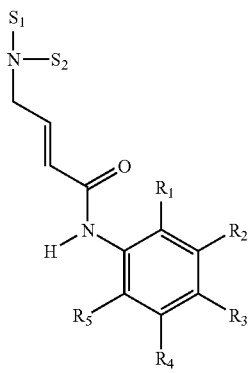

(II)

wherein
$R_1$, $R_2$, $R_3$, $R_4$, and $R_0$ are independently selected from the group consisting of —H, —CN, alkyl, alkoxy, vinyl, alkenyl, formyl, —$CF_3$, —$CCl_3$, halide, —$C_6H_5$, amide, acyl, ester, amino, thioalkoxy, phosphino, and combinations thereof;
or, taken together, $R_1$ and $R_2$, $R_2$ and $R_3$, $R_3$ and $R_4$, or $R_4$ and $R_0$, together with the carbon atoms to which they are attached, form an optionally substituted heteroaryl or cycloheteroalkyl; and
$S_1$ and $S_2$ are independently selected from the group consisting of hydrogen, alkyl, alkenyl, alkynyl, aralkyl, substituted or unsubstituted aryl, or $S_1$ and $S_2$ together with the nitrogen to which they are attached form a nitrogen containing heteroaryl, comprising:
(a) cooling a suspension of an acid addition salt of the compound of Formula (V);

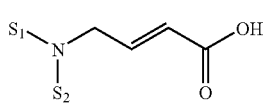

(V)

wherein $S_1$ and $S_2$ are defined above;
(b) adding a chlorinating agent to the suspension in step (a);
(c) warming and stirring the suspension in step (b) until the chlorinating agent is completely consumed;
(d) cooling the suspension in step (c);

(e) adding an aniline of formula (IV) dropwise to the suspension in step (d) until the concentration of the aniline is less than about 5%;

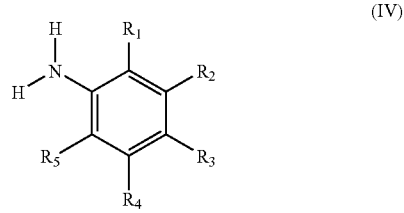

(IV)

wherein $R_1$, $R_2$, $R_3$, $R_4$ and $R_0$ are as defined above;
(f) adding an aqueous base to the suspension in step (e) to obtain a precipitate; and
(g) filtering and washing and drying the precipitate in step (f) to yield the compound of Formula (II).

For purposes of this invention a heteroaryl comprises a heterocyclic ring system of one to three fused rings, in which at least one ring may have an aromatic character and contains 1 to 4 heteroatoms the same or different selected from the group consisting of S, N, and O. The remaining rings of the ring system may be fully unsaturated, partially saturated, or fully saturated. Each ring comprises three to ten members. Preferred heteroaryl groups are thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, pteridine, carbazole, phenanthridine, acridine, perimidine, phenanthroline, phenazine, phenothiazine, furazan, phenoxazineand pyrrolidine. The heteroaryl can be independently substituted at one or more positions. Preferred substituents are halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, acyl, aldehyde, ester, a cycloheteroalkyl, an aromatic or heteroaromatic moiety, —CN, or Y.

Cycloheteroalkyl as used herein refers to a 5 to 9 membered saturated or unsaturated mono or bi-cyclic ring having 1 or 2 heteroatoms selected from N, N($C_1$–$C_6$ alkyl), S or O. Preferred cycloheteroalkyl groups are oxolane, thiolane, oxazole, piperidine, piperazine and morpholine. The cycloheteroalkyl can be independently substituted at one or more positions. Preferred substituents are halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a cycloheteroalkyl, an aromatic or heteroaromatic moiety and —CN.

When the heteroaryl is substituted with Y, wherein Y is —NH, —O—, —S—, or —NR—, wherein R is an alkyl of 1–6 carbon atoms, at one position on the ring there is further substitution on the —NH, —O—, —S—, or —NR— with a ($CH_2$)n-X group. For purposes of this invention n is 0–1 and "X" is cycloalkyl of 3 to 7 carbon atoms, which may be optionally substituted with one or more alkyl of 1 to 6 carbon atoms; or is a pyridinyl, pyrimidinyl, or phenyl ring; wherein the pyridinyl, pyrimidinyl, or phenyl ring may be optionally mono- di-, or tri-substituted with substituents independently selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, benzoylamino, and —Q—$(CH_2)_m$Ar, wherein Q is selected from O, NH, N($C_1$–$C_6$ alkyl) or S, m is 0, 1 or 2, and Ar is phenyl or pyridyl optionally substituted with one to three moieties independently selected from halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms and benzoylamino.

The alkyl portion of the alkyl, alkoxy, alkanoyloxy, alkoxymethyl, alkanoyloxymethyl, alkylsulphinyl, alkylsulphonyl, alkylsulfonamido, carboalkoxy, carboalkyl, alkanoylamino aminoalkyl, alkylaminoalkyl, N,N-dicycloalkylaminoalkyl, hydroxyalkyl, and alkoxyalkyl substituents include both straight chain as well as branched carbon chains.

The cycloalkyl portions of N-cycloalkyl-N-alkylaminoalkyl and N,N-dicycloalkylaminoalkyl substituents include both simple carbocycles as well as carbocycles containing alkyl substituents.

The alkenyl portion of the alkenyl, alkenoyloxymethyl, alkenyloxy, alkenylsulfonamido, substituents include both straight chain as well as branched carbon chains and one or more sites of unsaturation.

The alkynyl portion of the alkynyl, alkynoyloxymethyl, alkynylsulfonamido, alkynyloxy, substituents include both straight chain as well as branched carbon chains and one or more sites of unsaturation.

For purposes of this invention tri-alkylsilyl applies to alkyl (as hereinbefore defined) derivatives of the silyl group, $R_3Si$, wherein each R may be the same or different. Preferably, tri-alkylsilyl is trimethylsilyl.

Carboxy is defined as a —$CO_2H$ radical.

Carboalkoxy of 2–7 carbon atoms is defined as a —$CO_2R''$ radical, where R" is an alkyl radical of 1–6 carbon atoms.

Carboalkyl is defined as a —COR" radical, where R" is an alkyl radical of 1–6 carbon atoms.

Alkanoyloxy is defined as a —OCOR" radical where R" is an alkyl radical of 1–6 carbon atoms.

Alkanoyloxymethyl is defined as R"$CO_2CH_2$ radical where R" is an alkyl radical of 1–6 carbon atoms.

Alkoxymethyl is defined as R"$OCH_2$ radical where R" is an alkyl radical of 1–6 carbon atoms.

The term "vinyl" is defined as $CH_2$=CH and derivatives formed by substitution.

"Acyl" is a radical of the formula —(C=O) alkyl or —(C=O) perfluoroalkyl wherein the alkyl radical or perfluoroalkyl radical is 1 to 7 carbon atoms; preferred examples include but are not limited to, acetyl, propionyl, butyryl, trifluoroacetyl.

Alkylsulphinyl is defined as R"SO radical, where R" is an alkyl radical of 1–6 carbon atoms. Alkylsulphonyl is defined as R"$SO_2$ radical, where R" is an alkyl radical of 1–6 carbon atoms. Alkylsulfonamido, alkenylsulfonamido, alkynylsulfonamido are defined as R'''$SO_2$NH radical, where R''' is an alkyl radical of 1–6 carbon atoms, an alkenyl radical of 2–6 carbon atoms, or an alkynyl radical of 2–6 carbon atoms. N-alkylcarbamoyl is defined as R"NHCO radical, where R" is an alkyl radical of 1–6 carbon atoms. N,N-dialkylcarbamoyl is defined as R" R'NCO radical, where R" is an alkyl radical of 1–6 carbon atoms, R' is an alkyl radical of 1–6 carbon atoms and R', and R" may be the same or different.

For the purposes of this invention, $R_1$, $R_2$, $R_3$, $R_4$ and $R_0$ are each, independently, hydrogen, halogen, alkyl of 1–6 carbon atoms, alkenyl of 2–6 carbon atoms, alkynyl of 2–6 carbon atoms, alkenyloxy of 2–6 carbon atoms, alkynyloxy of 2–6 carbon atoms, hydroxymethyl, halomethyl, alkanoyloxy of 1–6 carbon atoms, alkenoyloxy of 3–8 carbon atoms, alkynoyloxy of 3–8 carbon atoms, alkanoyloxymethyl of 2–7 carbon atoms, alkenoyloxymethyl of 4–9 carbon atoms, alkynoyloxymethyl of 4–9 carbon atoms, alkoxymethyl of 2–7 carbon atoms, alkoxy of 1–6 carbon atoms, alkylthio of 1–6 carbon atoms, alkylsulphinyl of 1–6 carbon atoms, alkylsulphonyl of 1–6 carbon atoms, alkylsulfonamido of 1–6 carbon atoms, alkenylsulfonamido of 2–6 carbon atoms, alkynylsulfonamido of 2–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzyl, amino, hydroxyamino, alkoxyamino of 1–4 carbon atoms, alkylamino of 1–6 carbon atoms, dialkylamino of 2 to 12 carbon atoms, aminoalkyl of 1–4 carbon atoms, N-alkylaminoalkyl of 2–7 carbon atoms, N,N-dialkylaminoalkyl of 3–14 carbon atoms, phenylamino, benzylamino,

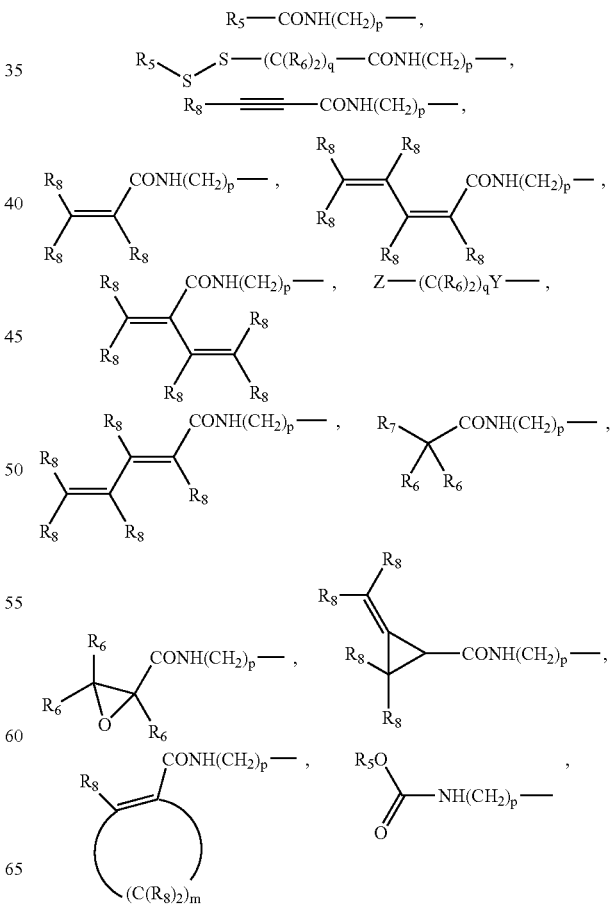

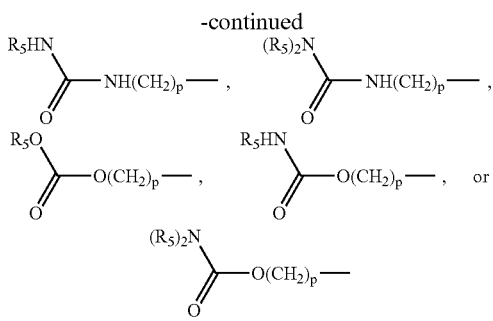

R₅ is alkyl of 1–6 carbon atoms, alkyl optionally substituted with one or more halogen atoms, phenyl, or phenyl optionally substituted with one or more halogen, alkoxy of 1–6 carbon atoms, trifluoromethyl, amino, nitro, cyano, or alkyl of 1–6 carbon atoms groups;

R₆ is hydrogen, alkyl of 1–6 carbon atoms, or alkenyl of 2–6 carbon atoms;

R₇ is chloro or bromo;

R₈ is hydrogen, alkyl of 1–6 carbon atoms, aminoalkyl of 1–6 carbon atoms, N-alkylaminoalkyl of 2–9 carbon atoms, N,N-dialkylaminoalkyl of 3–12 carbon atoms, N-cycloalkylaminoalkyl of 4–12 carbon atoms, N-cycloalkyl-N-alkylaminoalkyl of 5–18 carbon atoms, N,N-dicycloalkylaminoalkyl of 7–18 carbon atoms, morpholino-N-alkyl wherein the alkyl group is 1–6 carbon atoms, piperidino-N-alkyl wherein the alkyl group is 1–6 carbon atoms, N-alkyl-piperidino-N-alkyl wherein either alkyl group is 1–6 carbon atoms, azacycloalkyl-N-alkyl of 3–11 carbon atoms, hydroxyalkyl of 1–6 carbon atoms, alkoxyalkyl of 2–8 carbon atoms, carboxy, carboalkoxy of 1–6 carbon atoms, phenyl, carboalkyl of 2–7 carbon atoms, chloro, fluoro, or bromo;

Z is amino, hydroxy, alkoxy of 1–6 carbon atoms, alkylamino wherein the alkyl moiety is of 1–6 carbon atoms, dialkylamino wherein each of the alkyl moieties is of 1–6 carbon atoms, morpholino, piperazino, N-alkylpiperazino wherein the alkyl moiety is of 1–6 carbon atoms, or pyrrolidino;

m=1–4, q=1–3, and p=0–3;

Any of the substituents $R_1$, $R_2$, $R_3$, $R_4$ or $R_0$ that are located on contiguous carbon atoms can together be the divalent radical —O—C(R₈)₂—O—.

For purposes of this invention, an azacycloalkyl-N-alkyl substituent refers to a monocyclic heterocycle that contains a nitrogen atom on which is substituted a straight or branched chain alkyl radical. A morpholino-N-alkyl substituent is a morpholine ring substituted on the nitrogen atom with a straight or branch chain alkyl radical. A piperidino-N-alkyl substituent is a piperidine ring substituted on one of the nitrogen atoms with a straight or branch chain alkyl radical. A N-alkyl-piperidino-N-alkyl substituent is a piperidine ring substituted on one of the nitrogen atoms with a straight or branched chain alkyl group and on the other nitrogen atom with a straight or branch chain alkyl radical.

For purposes of this invention the term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone. More preferred alkyl groups are straight or branched chain having from 1 to 10 carbon atoms. Likewise, preferred cycloalkyls have from 3–10 carbon atoms in their ring structure. Moreover, the term "alkyl" as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an ester, a formyl, or a ketone), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF, —CN and the like.

For purposes of this invention "alkynyl" includes unsaturated aliphatic groups analogous in length and possible substitution to the alkyls described above, but that contain at least one triple bond, and include both straight or branched carbon chain of 2–6 carbon atoms.

For purposes of this invention "alkenyl" is defined as a aliphatic hydrocarbon that contains at least one carbon-carbon double bond and includes both straight and branched carbon chains of 2–6 carbon atoms in all possible configurational isomers, for example cis and trans, and includes ethenyl, 3-hexen-1-yl and the like. Exemplary substituted alkyls are described below. The term "aralkyl", as used herein, refers to an alkyl group substituted with an aryl group (e.g., an aromatic or heteroaromatic group).

Cycloalkenyl, as used herein, refers to a non-aromatic carbocycle of 3 to 10 carbon atoms with at least one carbon-carbon double bond in the ring.

For purposes of this invention the term "aryl" is defined as an aromatic carbocyclic moiety and may be substituted or unsubstituted. Preferred aryl groups have 6 to 14 carbon atoms. Particularly preferred aryl groups are phenyl and napthyl. The aromatic ring can be optionally independently mono-, di-, tri- or tetra-substituted. Preferred substituents are selected from the group consisting of, halogen, azide, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moietiesand —CN. The term "aryl" also includes polycyclic ring systems having two or more rings in which two or more carbons are common to two adjoining rings (the rings are "fused") wherein at least one of the carbocyclic rings is aromatic, e.g., the other rings can be cycloalkyls, cycloalkenyls, cycloalkynyls, and/or aryls.

Aralkyl, as used herein, refers to the moiety -alkyl-aryl, wherein aryl and alkyl are as previously defined. Benzyl is a preferred aralkyl group.

Ester, as used herein, refers to the group —OC(O)(C₁–C₆ alkyl).

In one embodiment of this invention the alkyl, alkenyl and alkynyl groups can be substituted with such substituents as phenyl, substituted phenyl, hydroxy, halogen, alkoxy, thioalkyl, carboxy, alkoxycarbonyl and acyl.

The compounds of this invention may include a "divalent group" defined herein as a linking group, for example, CH₂CH₂.

The compounds of this invention may contain one or more asymmetric carbon atom and may thus give rise to stereoisomers, such as enantiomers and diastereomers. While shown without respect to stereochemistry the compounds of the present invention include all the individual possible stereoisomers; as well as the racemic mixtures and other mixtures of R and S stereoisomers (scalemic mixtures which are mixtures of unequal amounts of enantiomers) and pharmaceutically acceptable salts thereof. It should be noted that stereoisomers of the invention having the same relative configuration at a chiral center may nevertheless have different R and S designations depending on the substitution at the indicated chiral center. Some of the compounds of this invention may contain one or more double bonds; in such cases, the compounds of this invention include each of the possible configurational isomers as well as mixtures of these isomers.

Salts of the compounds of this invention and intermediates can be formed from organic and inorganic bases. For example alkali metal salts: sodium, lithium, or potassium and N-tetraalkylammonium salts such as N-tetra-butylammonium salts.

When a compound of this invention or an intermediate contains a basic moiety, acid addition salts can be formed from organic and inorganic acids. For example salts can be formed from acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known protic acids. In a preferred embodiment of this invention the acid addition salt is a hydrochloride salt.

The term "heteroatom" as used herein means an atom of any element other than carbon or hydrogen. Preferred heteroatoms are nitrogen, oxygen, sulfur and phosphorous.

As used herein, the term "nitro" means $-NO_2$.; the term "halogen" designates $-F$, $-Cl$, $-Br$ or $-I$; the term "sulfhydryl" means $-SH$; the term "hydroxyl" means $-OH$; and the term "sulfonyl" means $-SO-$.

The terms "amine", "amino", and "amide" are art recognized and refer to both unsubstituted and substituted amines.

The term "alkylthio" refers to an alkyl group, as defined above, having a sulfur radical attached thereto. In preferred embodiments, the "alkylthio" moiety is represented by one of $-S$-alkyl, $-S$-alkenyl, $-S$-alkynyl, and $-S-$. Representative alkylthio groups include methylthio, ethylthio, and the like.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. The term "thioalkoxy" refers to an alkoxy group as defined, having a sulfur radical attached thereto.

Substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The abbreviations Me, Et, Ph, Tf, Nf, Ts, Ms, and dba represent methyl, ethyl, phenyl, trifluoromethanesulfonyl, nonafluorobutanesulfonyl, p-toluenesulfonyl, methanesulfonyl, and dibenzylideneacetone, respectively. A more comprehensive list of the abbreviations utilized by organic chemists of ordinary skill in the art appears in the first issue of each volume of the Journal of Organic Chemistry; this list is typically presented in a table entitled Standard List of Abbreviations. The abbreviations contained in said list, and all abbreviations utilized by organic chemists of ordinary skill in the art are hereby incorporated by reference.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

Unless otherwise specified, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

In one embodiment of this invention cooling a suspension occurs at about $-10°$ C. to about $25°$ C. In a preferred embodiment the cooling is done at a temperature of about $0°$ C. to about $10°$ C.

In an embodiment of this invention warming the suspension occurs at $20-30°$ C.

For purposes of this invention an aqueous base or base can be for example sodium carbonate, bicarbonate, sodium hydroxide, potassium bicarbonate and carbonate or the like.

The term aniline, as used herein, refers to an aryl or heteroaryl moiety bearing an amino group on a ring atom. Preferably, the amino group is primary ($NH_2$). In a preferred embodiment of this invention the aniline is;

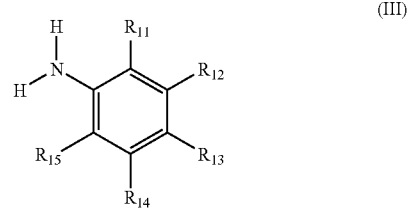

(III)

wherein $R_{11}$, $R_{12}$, $R_{13}$, $R_{14}$, $R_{15}$, are selected from the group consisting of H, CN, alkyl, alkoxy, vinyl, alkenyl, formyl, $CF_3$, $CCl_3$, halide, $C_6H_5$, amide, acyl, ester, alkoxy, amino, thioalkoxy, phosphino, and combinations thereof;

wherein when $R_{11}$, $R_{12}$, $R_{13}$, or $R_{14}$ are O, N or S the O, N, or S together with the carbon to which it is attached and the adjacent carbon form a substituted or unsubstituted heteroaryl.

In a preferred embodiment the aniline is 4-[4-benzyloxy-3-chloro]amino-6-amino-3-cyano-7-ethoxyquinoline. In another embodiment of the invention the aniline is 4-(4-(2-pyridylmethoxy)-3-chloro)amino-3-cyano-7-ethoxyquinoline. In yet another embodiment of the invention the aniline is [4-(3-chloro-4-fluoro-phenylamino)-3-cyano-7-ethoxyquinoline.

The following experimental details are set forth to aid in an understanding of the invention, and are not intended, and should not be construed to limit in any way the invention set forth in the claims that follow thereafter.

DETAILED DESCRIPTION OF THE INVENTION

The preparation of the compounds of Formula II is described in Scheme I wherein:

A compound of A reacts with 4-(dimethylamino)-2-butenoyl chloride (hydrochloride) (I) at a temperature from about 0° C. to about 24° C. in a polar aprotic solvent which yields the compound of Formula (II). The compound of Formula (II) is collected as a solid after the addition of aqueous sodium bicarbonate. One recrystallization of said solid from tetrahydrofuran (THF)-acetonitrile (CH$_3$CN) yields a compound of Formula (II) with >95% purity and a 85% recovery. A second recrystallization from tetrahydrofuran (THF)-acetonitrile (CH$_3$CN) yields a compound of Formula 3 with >98% purity and an 85% recovery.

Reaction Scheme Example 1:

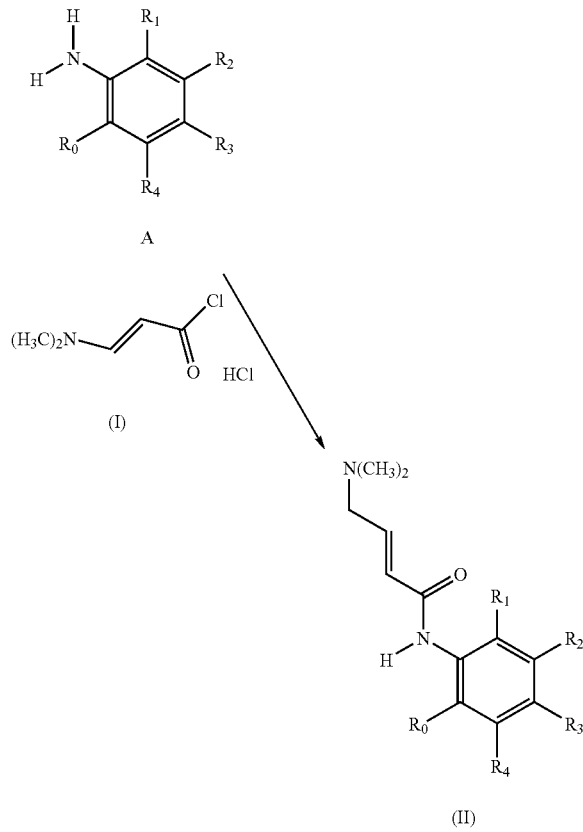

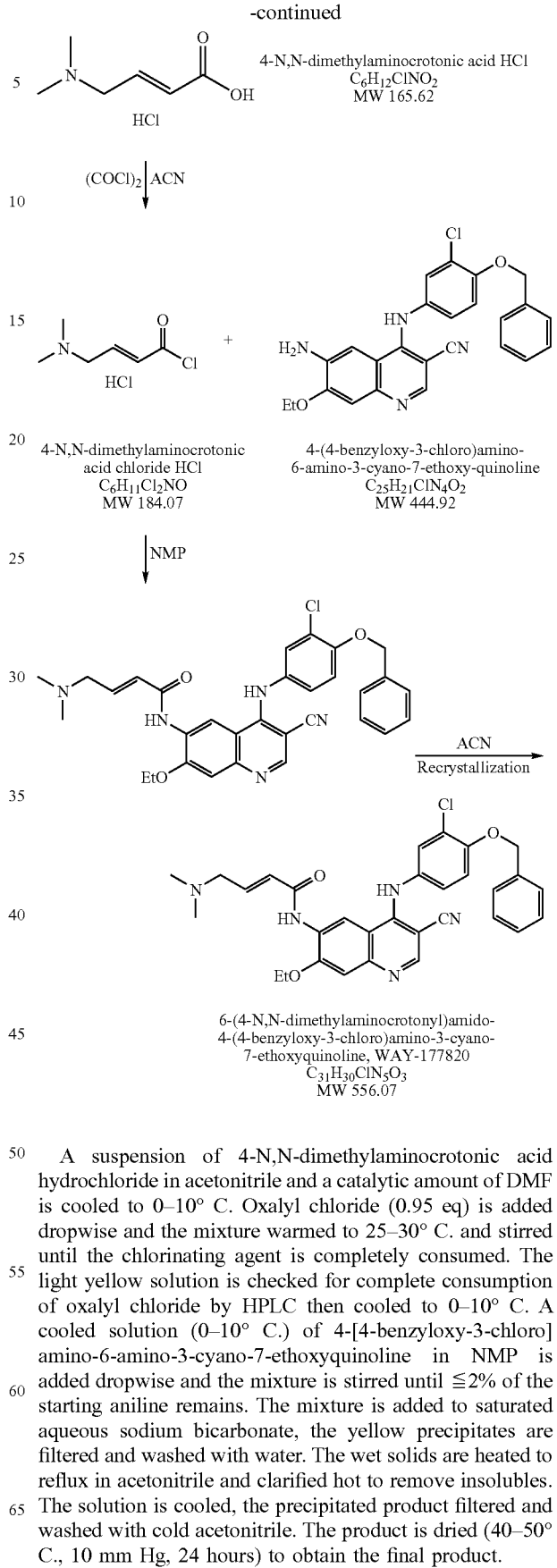

A suspension of 4-N,N-dimethylaminocrotonic acid hydrochloride in acetonitrile and a catalytic amount of DMF is cooled to 0–10° C. Oxalyl chloride (0.95 eq) is added dropwise and the mixture warmed to 25–30° C. and stirred until the chlorinating agent is completely consumed. The light yellow solution is checked for complete consumption of oxalyl chloride by HPLC then cooled to 0–10° C. A cooled solution (0–10° C.) of 4-[4-benzyloxy-3-chloro]amino-6-amino-3-cyano-7-ethoxyquinoline in NMP is added dropwise and the mixture is stirred until ≦2% of the starting aniline remains. The mixture is added to saturated aqueous sodium bicarbonate, the yellow precipitates are filtered and washed with water. The wet solids are heated to reflux in acetonitrile and clarified hot to remove insolubles. The solution is cooled, the precipitated product filtered and washed with cold acetonitrile. The product is dried (40–50° C., 10 mm Hg, 24 hours) to obtain the final product.

Reaction Scheme Example 2:

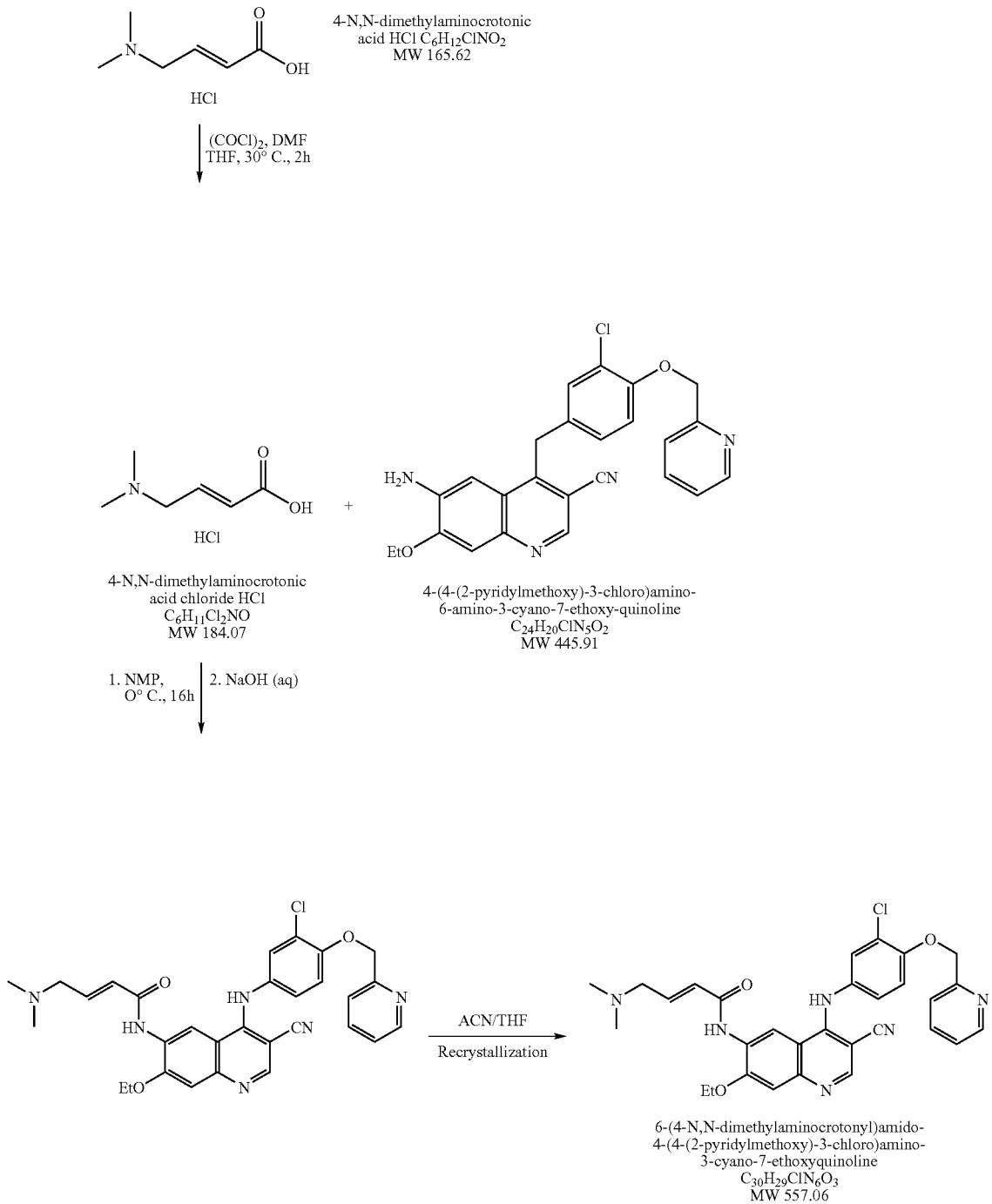

A solution of 4-N,N-dimethylaminocrotonic acid hydrochloride in tetrahydrofuran (THF) and a catalytic amount of dimethylformamide (DMF) is cooled to 0–5° C. Oxalyl chloride (0.95 eq) is added dropwise and the mixture warmed to 25–30° C. and stirred until the chlorinating agent is completely consumed. The orange solution is checked for complete consumption of oxalyl chloride by high-pressure liquid chromatography (HPLC) then cooled to 0–5° C. A solution of 4-[4-(2-pyridylmethoxy)-3-chloro]amino-6-amino-3-cyano-7-ethoxyquinoline is added dropwise and the mixture is stirred until ≦0.5% of the starting aniline remains. The reaction is quenched with water and the mixture warmed to 40° C. Aqueous sodium hydroxide is added to bring the pH to 10–11. The resulting precipitates are filtered hot and washed with water. The wet solids are heated to reflux (70–75° C.) in acetonitrile:THF (1:5:1) and the solution cooled slowly to room temperature. The product is filtered and washed with acetonitrile:THF. The product is dried (50° C., 10 mm Hg, 24 hours) to 80–85% yield.

Reaction Scheme Example 3:

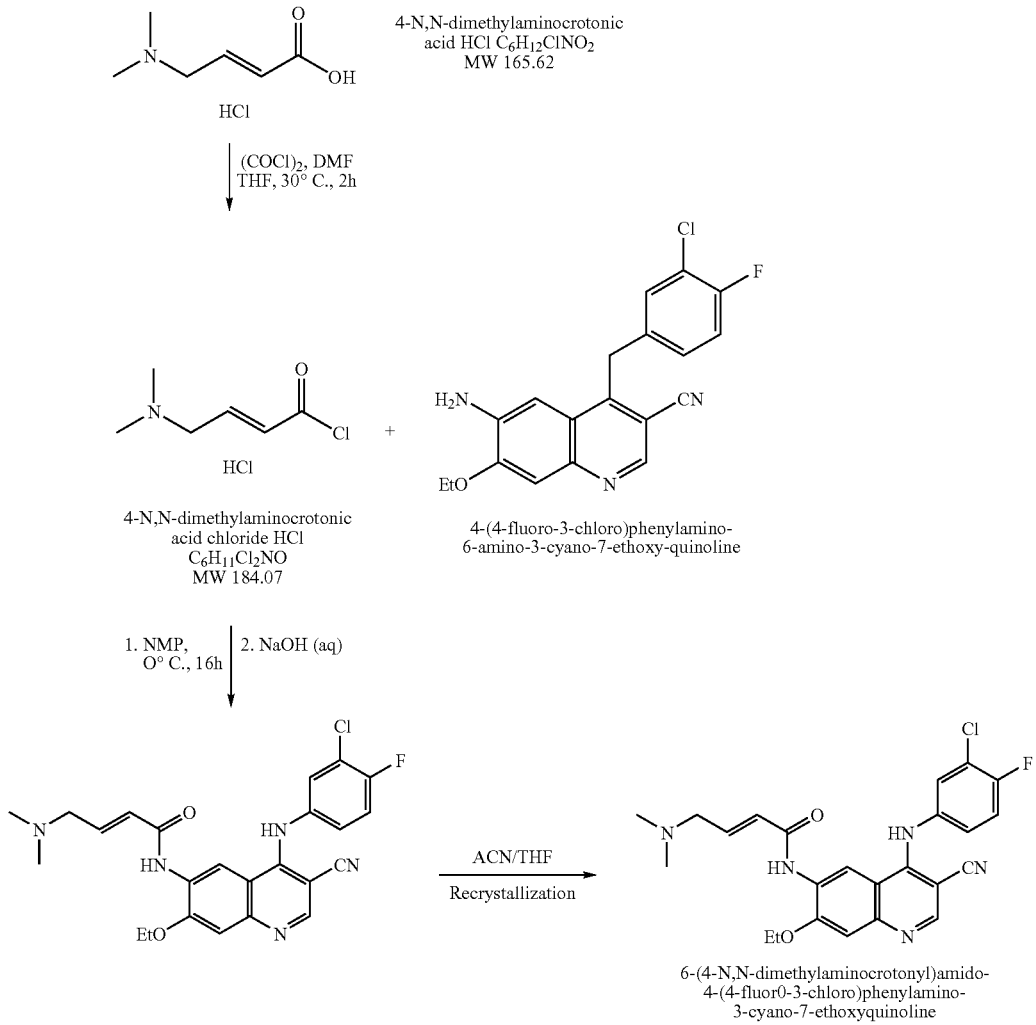

4-Dimethylamino-but-2-enoic acid [4-(3-chloro-4-fluoro-phenylamino)-3-cyano-7-ethoxy-quinolin-6-yl]amide

4-(Dimethylamino)-2-butenoyl chloride hydrochloride

A 1 L multi-neck flask equipped with agitator, thermometer, addition funnel, and nitrogen protection is charged with acetonitrile (0.67 kg, 0.85 L) followed by adding dimethylformamide (0.00086 kg, 0.91 mL, d=0.944 g/mL). At ambient temperature, is added 4-dimethylaminocrotonic acid hydrochloride (0.0709 kg) and the mixture stirred until homogeneous. Cool the reaction mixture to (0–10° C.) and add oxalyl chloride (0.0473 kg, 0.0325 L, d=1.45 g/mL) dropwise over (20 minutes) at (0–10° C.) followed by a rinse with acetonitrile (0.02 kg, 0.03 L). The temperature (0–10° C.) is maintained for about (20 minutes). The temperature of the reaction mixture is adjusted to (22–26° C.) over (20 minutes) and maintained over (2 hours). The temperature of reaction mixture is adjusted to (40–45° C.) and held for about (5 minutes). Cool the light suspension to about (20–25° C.) and check for reaction completion by high-pressure liquid chromatography (HPLC). The reaction is complete when there is ≦15% of the starting material (4-dimethylaminocrotonic acid hydrochloride) present and/or ≦2% of oxalyl chloride (detected as the dimethyl oxalate).

4-Dimethylamino-but-2-enoic acid [4-(3-chloro-4-fluoro-phenylamino)-3-cyano-7-ethoxy-quinolin-6-yl]-amide (Crude)

A 3 L multi-neck flask equipped with agitator, thermometer, dip tube, and nitrogen protection is charged N-methyl pyrrolidinone (0.77 kg, 0.75 L, d=1.033 g/mL). At ambient temperature is added 4-[3-chloro-4-fluorophenyl]amino-6-amino-3-cyano-7-ethoxy quinoline (0.0748 kg). The reaction mixture is heated to 40–45° C. and maintained for about (15 minutes). The reaction mixture is cooled to (0–10° C.) and the light suspension of 4-(dimethylamino)-2-butenoyl chloride hydrochloride in CH$_3$CN added via dip tube and positive nitrogen pressure, over (30–45 minutes) while maintaining the temperature (0–10° C.) for at least (2 hours). Reaction completion is monitored by HPLC. The reaction is complete when there is ≦2% of the starting material (4-[3-chloro-4-fluorophenyl]amino-6-amino-3-cyano-7-ethoxy quinoline) present. To a 12 L multi-neck flask equipped with agitator, thermometer, dip tube, and nitrogen protection is charged with water (2.61 kg, 2.61 L) and sodium bicarbonate (0.209 kg) with stirring until a solution is obtained followed by cooling to (20–24° C.) to which is transferred the reaction mixture above which contains ≦2% of the starting material (4-[3-chloro-4-fluorophenyl]amino-6-amino-3-cyano-7-ethoxy quinoline), via dip tube and positive nitrogen pressure, to the 12 L flask over about (45–60 minutes) while maintaining the temperature at (20–24° C.). The temperature is maintained at (20–24° C.) for at least (1 hour). Filter the reaction mixture on a Buchner funnel, rinse with water (3×0.40 kg, 3×0.40 L), and maintain suction until dripping stops. Dry the product in a vacuum oven at about (50° C.) and about (10 mm Hg) for about (28–30 hours). The yield is 78.5 g (86%) at 79.7% strength and 12.3% total impurities.

4-Dimethylamino-but-2-enoic acid [4-(3-chloro-4-fluoro-phenylamino)-3-cyano-7-ethoxy-quinolin-6-yl]-amide (Purified Small Scale)

First Crop:

A 6 L multi-neck flask equipped with agitator, condenser, temperature probe, and nitrogen protection is charged with acetonitrile (3.14 kg, 4.00 L) followed by adding 4-dimethylamino-but-2-enoic acid [4-(3-chloro-4-fluoro-phenylamino)-3-cyano-7-ethoxy-quinolin-6-yl]-amide (0.16 kg, 0.167 moles). Heat the mixture to (75–80° C.) and hold it for (1 hour). Cool the mixture to (70–75° C.) and filter on a pad of diatomaceous earth to remove inorganic salts. Wash the pad with acetonitrile (2×0.24 kg, 2×0.30 L), preheated to (70–75° C.). Concentrate the filtrate at (20–30 mm Hg) and a maximum temperature of (40–45° C.) to a volume of (1.2 L). To the concentrate (slurry) add prefiltered tetrahydrofuran (0.53 kg, 0.60 L). Heat to (65–70° C.) to obtain a complete solution. Cool the mixture to (40–45° C.) over (0.3 hours). Add seeds and continue cooling to (20–25° C.) over (1 hour). Hold at (20–25° C.) for a minimum of (18 hours). Collect the solid on a Buchner funnel and wash the collected solid with a prefiltered and precooled at (0–5° C.) mixture of acetonitrile/tetrahydrofuran (2/1 by volume) (2×0.06 kg, 2×0.08 L). Dry the product in a vacuum oven at (50° C.) and (10 mm Hg) for (48 hours) to a loss on drying (LOD) of less than (0.5%). All washes and concentrates (mother liquors) are saved for further purification.

Second Crop:

A 3 L multi-neck flask equipped with agitator, temperature probe, nitrogen protection, and charge with the mother liquors and washes from above. Concentrate by distillation at (20–30 mm Hg) and a maximum temperature of (40–45° C.) to a volume of (0.50 L). Collect the solid on a Buchner funnel and wash the solid with prefiltered acetonitrile (0.04 kg, 0.05 L). Dry the solid product in a vacuum oven at (50° C.) and (10 mm Hg) for (18 hours). A 1 L multi-neck flask equipped with agitator, condenser, temperature probe, nitrogen protection and charge with prefiltered acetonitrile (0.47 kg, 0.60 L), and the collected solid is heated as a suspension to (70–75° C.) over (0.5 hours). Add prefiltered tetrahydrofuran (0.03 kg, 0.03 L) to the suspension while maintaining the temperature at (70–75° C.). Cool the solution to (40–45° C.) and add seed crystals. Continue cooling to (20–25° C.) over (1 hour) and hold for (2 hours). Collect the resulting solid on a Buchner funnel and wash the collected solid with a prefiltered and precooled to (5° C.) mixture of acetonitrile/tetrahydrofuran (20/1 by volume) (2×0.02 kg, 2×0.03 L). Dry the collected solid in a vacuum oven at (50° C.) and (10 mm Hg) for (24 hours) to an LOD of less than (0.5%). The combined yield is 27.5 g+30.5 g (73%) in 96.2–98.4% strength and 1.5–1.7% total impurities by high pressure liquid chromatography (HPLC).

4-Dimethylamino-but-2-enoic acid [4-(3-chloro-4-fluoro-phenylamino)-3-cyano-7-ethoxy-quinolin-6-yl]-amide (Purified Larger Scale)

Acetonitrile, practical (34.0 kg) and 4-dimethylamino-but-2-enoic acid [4-(3-chloro-4-fluoro-phenylamino)-3-cyano-7-ethoxy-quinolin-6-yl]-amide (2.69 kg crude, 1.53 kg at 100% strength) are charged to a purged (100 L) reactor. Acetonitrile, practical (2.0 kg) is used as rinse for funnel and vessel walls. The brown suspension is heated at 70 to 76° C. using a jacket temperature not exceeding 85° C., then held at the latter temperature for a minimum of 45 minutes, not exceeding 60 minutes. The resulting suspension is then filtered on the warm-jacketed (70–76° C.) 14" Aurora filter, while maintaining the batch temperature at 70 to 76° C. The filtrates are collected by pump into a purged (100 L) receiver, while keeping their temperature below 50° C. The diatomaceous earth pad is then washed with warm (70 to 76° C.) acetonitrile, practical (3×2.5 kg). The filtrates and washes in (100 L) receiver are cooled to 20 to 26° C., then transferred into a stainless steel drum. Acetonitrile, practical (2.0 kg) is used as rinse. After cleaning and purging both vessels, the contents of the stainless steel drum is transferred into the (100 L) receiver. Acetonitrile, practical (2.0 kg) is used as a rinse. The batch is heated at 70 to 76° C. without exceeding jacket temperature of 85° C. The batch is filtered by pump through a 1.0 micron single cartridge filter, while maintaining the contents at 70 to 76° C. Warm (70–76° C.) acetonitrile, practical (4.0 kg) is used as rinse for vessel, filters, pump and lines. The filtrate and rinse are collected and maintained below 50° C. The batch is adjusted to 10 to 16° C., then concentrated by vacuum distillation to 28 to 33 L volume: expected distillation temperature 20 to 30° C., distillate volume 32 to 37 L. The suspension is heated to 64 to 70° C. without exceeding jacket temperature of 85° C. The resulting solution is cooled to 40 to 46° C., then seeded using 4-dimethylamino-but-2-enoic acid [4-(3-chloro-4-fluoro-phenylamino)-3-cyano-7-ethoxy-quinolin-6-yl]-amide, purified (0.5 g). The mixture is cooled to 20 to 26° C. over 1 hour, then held at the latter temperature for a minimum of 2 hours. The suspension is then cooled at –3 to 3° C. over 1 hour, then held for a minimum of 1 hour. The solid product is collected on a 16" Buchner, then washed with cold (0–5° C.) acetonitrile-tetrahydrofuran (20–6 v/v) mixture (2×2.5 kg). The wet collected solid is recrystallized once more from acetonitrile-tetrahydrofuran (20–6 v/v) to desired purity. The material is dried in a vacuum oven first at 35 to 45° C. (target 40° C.) for 4 hours, liquid ring pump, then 45 to 55° C. (target 50° C.) for 4 hours. After high vacuum is applied at the latter temperature, until LOD <0.5% (90° C., 2 hours, full vacuum) and each of acetonitrile, tetrahydrofuran and 1-methyl-2-pyrrolidinone are below 0.2%. The purified drug substance is milled (Comil), then blended. The yield is 1.10 kg (70.1%, corrected for starting material). The strength of the material is 98.3% and a total impurities of 1.27%.

The preparation of 4-(dimethylamino)-2-butenoyl chloride (hydrochloride) (I) is described in Scheme II wherein but-2-enoic acid 7 is reacted with chlorotrimethylsilane in pyridine to afford trimethylsilylcrotonate 8 which is brominated with a brominating agent preferably N-bromosuccinimide under free radical conditions in the presence of light and peroxide in methylene chloride, acetonitrile, 1,2-dichloroethane, carbon tetrachloride or ethyl acetate to give trimethylsilyl-4-bromocrotonate 9. Reaction of trimethylsilyl-4-bromocrotonate 9 with dimethylamine in tetrahydrofuran at about 0–5° C. affords 4-dimethylaminocrotonic acid 10 isolated as the hydrochloride salt. Alternatively, 4-dimethylaminocrotonic acid 10 can be prepared by reaction of methyl or ethyl 4-bromocrotonate 11 with dimethylamine at 0 to 10° C. in tetrahydrofuran to give methyl or ethyl 4-dimethylaminocrotonate 12 which is hydrolyzed with aqueous base which includes sodium hydroxide in methanol as a cosolvent at about 40–45° C. to give 4-dimethylaminocrotonic acid 10 which is isolated to 4-dimethylaminocrotonic acid (hydrochloride) 10 with a solution of hydrogen chloride in isopropyl alcohol, and then chlorinated with a chlorinating agent preferably, but not limited to, oxalyl chloride in methylene chloride, tetrahydrofuran (THF) or acetonitrile in the presence of a catalytic amount of N,N-dimethylformamide to afford 4-(dimethylamino)-2-butenoyl chloride hydrochloride 2.

Trimethylsilyl-4-bromocrotonate

A stirred mixture of trimethylsilylcrotonate (131 g, 0.828 mol), N-bromosuccinimide (206 g, 1.16 mol), benzoyl peroxide (3.41 g, 0.141 mol) and carbon tetrachloride (1 L) is warmed to reflux (77° C.) under visible light for 5 hours. The mixture is cooled to room temperature and the precipitated solid is removed by filtration. The filtrate is concentrated to a residue, which is distilled under reduced pressure. The product fractions are collected at 93–106° C. (9–15 mmHg) to give 127 g of the title compound (65%). GC-MS purity is 83–89%, $^1$HNMR is consistent with expected structure.

SCHEME II:

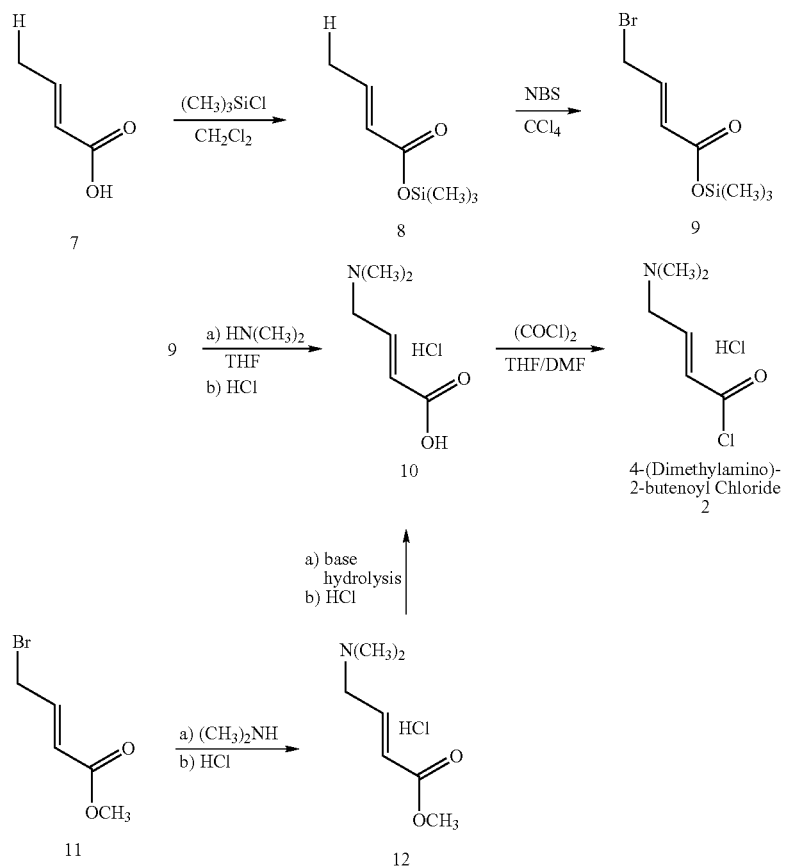

Trimethylsilylcrotonate

Pyridine (138 g, 1.74 mol) is added dropwise to a stirred solution of crotonic acid (125 g, 1.45 mol), and chlorotrimethylsilane (189 g 1.74 mol) in ether (1.5 l) at room temperature. The reaction mixture is allowed to stir at room temperature overnight and the precipitate is removed by filtration. The filtrate is concentrated and the residue is distilled under reduced pressure. The product fraction is collected at 58–70° C. (25 mmHg) to give 180 g of the title compound (79%). GC-MS purity is 93.4%, $^1$HNMR is consistent with the structure.

4-Dimethylaminocrotonic acid

4-Dimethylaminocrotonic acid

A solution of 211 ml of dimethylamine (2M in tetrahydrofuran, 0.422 moles) is added dropwise to a solution of 50 g trimethylsilyl-4-bromocrotonate (0.211 moles, 75.9% by GC-MS) in 250 ml of tetrahydrofuran at 0–5° C. under $N_2$. The reaction mixture is stirred at room temperature for 30 minutes. A white solid by-product is removed by filtering and 2 ml water is added to the filtrate followed by seeding.

The crystals formed are filtered and washed with ether to give 18.3 g (from two crops) of the desired product as off-white solid. Yield is 67.2% (98% purity by GC-MS, NMR is consistent with the expected structure).

4-Dimethylaminocrotonic acid hydrochloride

A solution of sodium hydroxide (3.35 g, 0.0838 mol) in water (24 mL) is added to a stirred solution of methyl 4-dimethylaminocrotonate (12 g, 0.0838 mol) in methanol (100 mL). The reaction mixture is warmed to 40–45° C. for 1 hour then cooled to room temperature. Hydrochloric acid (5N) is added to bring the pH of the reaction mixture to 1–2. The reaction mixture is concentrated under reduced pressure to a thick oil. Ethanol (anhydrous, 100 mL) is added and the solid (sodium chloride) is removed by filtration. The filtrate is concentrated under reduced pressure and product precipitation is induced by addition of 2-propanol (50 mL) to afford a solid which is collected to give the desired product (7.0 g, 50%). GC-MS purity is 86%. $^1$HNMR is consistent with expected structure.

Methyl 4-dimethylaminocrotonate

A solution of 120 ml of dimethylamine (2M in tetrahydrofuran, 0.24 moles) is added dropwise to a solution of 20 g methyl 4-bromocrotonate (85% purity, 0.095 moles) in 150 ml of tetrahydrofuran at 0–5° C. under $N_2$. The reaction mixture is stirred for 15 minutes at room temperature. Thin layer chromatography (TLC) (9:1 $CH_2Cl_2$:MeOH with few drops of triethylamine) showed residual methyl 4-bromocrotonate. The reaction mixture is heated to 40–45° C. for 15 minutes. A white solid by-product is removed by filtering and the filtrate is evaporated to give a yellow oil (14 g). The yellow oil is dissolved in 100 ml $CH_2Cl_2$ and washed with $H_2O$ twice. The aqueous layer is back extracted with 100 ml $CH_2Cl_2$. The $CH_2Cl_2$ layers are combined, dried over $MgSO_4$ and filtered. The filtrate is evaporated to give the desired product as an oil. Yield is 88%. NMR indicated desired product with trace methyl 4-bromocrotonate.

Methyl 4-dimethylaminocrotonate hydrochloride

To a 3 L multi-neck flask equipped with agitator, thermometer, addition funnel, and nitrogen protection is added tetrahydrofuran (0.71 kg, 0.80 L). To the stirred mixture is added (0.20 kg, 0.13 L, d=1.522 g/mL) methyl 4-bromocrotonate with a rinse of tetrahydrofuran (0.18 kg, 0.20 L). The reaction mixture is stirred and the solution cooled to (0–10° C.). A 2.0 M solution of dimethylamine in tetrahydrofuran is added over (1 hour 15 minutes) followed by keeping the temperature (0–10° C.) for at least 30 minutes. The reaction is checked for completion by TLC and is complete when there is ≦2% detectable starting material (methyl 4-bromocrotonate) present. The cold reaction mixture is filtered on a Buchner funnel into a 3 L multi-neck flask, rinse with pre-chilled (0–10° C.) tetrahydrofuran (2×0.18 kg, 2×0.20 L). The solution is evaporated under reduced pressure (125–200 mm Hg) at a maximum temperature of (40° C.) to a volume of about (200 mL). Isopropanol (0.22 kg, 0.28 L) is added and the mixture cooled to (0–10° C.). Add over (45 minutes) a 10% w/w solution of HCl in isopropanol until the pH is (2.0–3.0) while maintaining the temperature at (0–10° C.) for at least (30 minutes) after addition. The cold mixture is filtered on a Buchner funnel, and the collected solid rinsed with isopropanol (2×0.12 kg, 2×0.15 L) suction dry followed by drying the product in a vacuum oven at about (50° C.) and about (10 mm Hg) for about (18–20 hours) to a loss on drying of less than (1%). The yield is 126 g (74%). Strength: 97.6%

4-Dimethylaminocrotonic acid hydrochloride (Small Scale)

A sodium hydroxide solution (3.35 g in 25 ml of water, 0.084 moles) is added dropwise to a solution of 12 g methyl 4-dimethylaminocrotonate (0.084 moles) in 100 ml methyl alcohol at room temperature. The reaction mixture is heated to 40–45° C. for 1 hour then cooled to room temperature. The pH is adjusted to about 1~2 with 5 N HCl. The mixture was concentrated to a thick oil, which is triturated with dehydrated alcohol to form a solid. The solid by-product is filtered and the filtrate is evaporated to an oil, which is triturated with isopropyl alcohol to afford 7.0 g of white solid product. Yield is 50% with the purity 86.3% by GC-MS.

4-Dimethylaminocrotonic acid hydrochloride (Larger Scale)

A 2 L multi-neck flask equipped with agitator, thermometer, addition funnel, and nitrogen protection is charged with ethanol (0.39 kg, 0.50 L) followed by adding methyl 4-dimethylamino crotonate hydrochloride (0.125 kg) with a final ethanol rinse (0.10 kg, 0.125 L). The stirred suspension is cooled to (0–10° C.) and while maintaining the temperature, sodium hydroxide (50%) (0.11 kg, 0.072 L, d=1.53 g/mL) is added over 20 minutes. A slight exotherm is observed with a temperature increase and the mixture turns yellow. The temperature is maintained for at least 15 minutes followed by warming to (18–22° C.) and maintaining the temperature for at least (4 hours). The progress of the reaction is followed by thin layer chromatography (TLC.). The reaction is complete when there is ≦2% detectable starting material (methyl 4-dimethylaminocrotonate hydrochloride) present. The reaction mixture is cooled to about (0–10° C.) and while maintaining the temperature a 11% w/w solution of HCl in isopropanol is added over (40 minutes) until the pH is adjusted to (2.0–3.0). After at least 30 minutes minimum the cold mixture is filtered on a Buchner funnel and the filter cake rinsed with ethanol (0–10° C.)(2×0.05 kg, 2×0.063 L). The filtrate is concentrated under reduced pressure (50–100 mm Hg) at a maximum temperature of (40° C.) to a concentrate of about (160–180 mL). To the concentrate is added isopropanol (0.049 kg, 0.063 L) and the mixture warmed to (35–40° C.) over (10 minutes). Acetone (0.10 kg, 0.13 L) is added over (20 minutes) while maintaining the temperature at about (35–40° C.). The mixture is seeded and then cooled to ambient temperature (20–25° C.) for at least (12–18 hours). Cool the mixture to (0–10° C.) and maintain the temperature for a minimum of (1 hour). Prepare a mixture of isopropanol (0.049 kg, 0.063 L) and acetone (0.10 kg, 0.13 L), stir to homogenize and cool to (0–10° C.). Filter the cold mixture on a Buchner funnel, rinse with (0–10° C.) isopropanol/acetone (2×0.074 kg, 2×0.096 L). Suction is maintained until dripping stops. Dry the product in a vacuum oven at about (50° C.) and about (10 mm Hg) for about (18–20 hours) to a loss on drying of less than (1%). The yield is 47 g (41%) at 92% strength and 1.33% total impurities.

4-(dimethylamino)-2-butenoyl chloride hydrochloride

A well stirred suspension of 4-dimethylaminocrotonic acid hydrochloride (5.0 g, 30 mmol) in cold (0° C.) THF (40 mL) and DMF (2 pipet drops) is treated with oxalyl chloride (3.15 mL, 36 mmol). Stirring at 20–25° C. for 3 hours is followed by cooling to 0° C. and holding for 30 minutes. Solids are collected on a Buchner funnel (under a blanket of nitrogen) and the cake is washed with cold (0° C.) THF (3×5 mL). The solid is dried under vacuum (~1 torr) at 40–50° C. for 3 hours to give 4.0 g of 4-dimethylaminocrotonoyl chloride hydrochloride. This material is characterized as its methyl ester by treatment of the solid with methanol.

Alternatively, 4-(dimethylamino)-2-butenoyl chloride hydrochloride can be prepared in acetonitrile and used as a suspension in acetonitrile for the next reaction.

What is claimed is:

1. A compound of Formula (I):

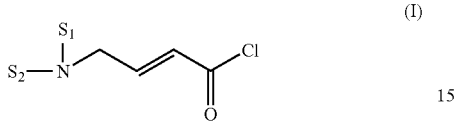

(I)

wherein
$S_1$ and $S_2$ are each independently, cycloalkyl, cycloalkenyl, alkenyl, alkynyl, aralkyl, substituted or unsubstituted aryl or heteroaryl, or $S_1$ and $S_2$ together with the nitrogen to which they are attached form a nitrogen containing heteroaryl or cycloheteroalkyl; or
an acid addition salt thereof.

2. The compound of claim 1 wherein the acid addition salt is a hydrochloride salt.

3. A process for the preparation of a compound of claim 1 comprising:
(a) reacting a 4-bromocrotonate with $S_1,S_2$—N—R wherein R is H, trialkylsilyl or alkali metal and $S_1$ and $S_2$ are as defined in claim 1 or an acid addition salt thereof to obtain the corresponding 4-$S_1,S_2$-aminocrotonate;
(b) hydrolyzing 4-$S_1,S_2$-aminocrotonate of step (a) in the presence of a base; and isolating as a corresponding hydrochloride salt; and
(c) chlorinating the compound of step (b) with a chlorinating agent to obtain the compound of claim 1.

4. A process of claim 3 wherein the chlorinating agent is oxalyl chloride.

5. A process for the preparation of a compound of Formula (II):

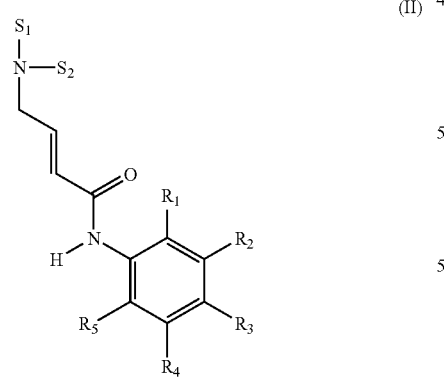

(II)

wherein
$R_1$, $R_2$, $R_3$, $R_4$, and $R_0$ are independently selected from the group consisting of —CN, alkyl, alkoxy, vinyl, alkenyl, formyl, —$CF_3$, —$CCl_3$, halide, —$C_6H_5$, amide, acyl, ester, amino, thioalkoxy, phosphino, and combinations thereof;
or, taken together, $R_1$ and $R_2$, $R_2$ and $R_3$, $R_3$ and $R_4$, or $R_4$ and $R_0$, together with the carbon atoms to which they are attached, form an optionally substituted heteroaryl or cycloheteroalkyl; and
wherein $S_1$, and $S_2$ are defined in claim 1, comprising:
(a) cooling a suspension of an acid addition salt of the compound of Formula (V);

$$S_1\text{—}\underset{\underset{S_2}{|}}{N}\text{—}CH=CH\text{—}C(=O)\text{—}OH \quad (V)$$

wherein $S_1$ and $S_2$ are defined in claim 1;
(b) adding a chlorinating agent to the suspension in step (a);
(c) warming and stirring the suspension in step (b) until the chlorinating agent is completely consumed;
(d) cooling the suspension in step (c);
(e) adding an aniline of formula (IV) dropwise to the suspension in step (d) until the concentration of the aniline is less than about 5%;

(IV)

wherein $R_1$, $R_2$, $R_3$, $R_4$ and $R_0$ are as defined above;
(f) adding an aqueous base to the suspension in step (e) to obtain a precipitate; and
(g) filtering and washing and drying the precipitate in step (f) to yield the compound of Formula (II).

6. The process of claim 5 wherein cooling comprises a temperature of –10 to 25° C.

7. The process of claim 6 wherein the cooling comprises a temperature of 0 to 10° C.

8. The process of claim 5 wherein the warming comprises a temperature of 20 to 30° C.

9. The process of claim 5 wherein the base is selected from sodium carbonate, sodium bicarbonate, sodium hydroxide, potassium bicarbonate, and potassium carbonate.

10. The process of claim 9 wherein the base is sodium bicarbonate.

11. The process of claim 5 wherein the aniline is 4-[4-benzyloxy-3-chloro]amino-6-amino-3-cyano-7-ethoxyquinoline, 4-(4-(2-pyridylmethoxy)-3-chloro)amino-3-cyano-7-ethoxyquinoline or [4-(3-chloro-4-fluorophenylamino)-3-cyano-7-ethoxy-quinoline.

12. The process of claim 5 wherein the concentration of the aniline is less than 2%.

* * * * *

UNITED STATES PATENT AND TRADEMARK OFFICE
CERTIFICATE OF CORRECTION

PATENT NO. : 7,126,025 B2
APPLICATION NO. : 10/758187
DATED : October 24, 2006
INVENTOR(S) : Considine et al.

It is certified that error appears in the above-identified patent and that said Letters Patent is hereby corrected as shown below:

(1) Col. 3, lines 20-34 delete the following structure:

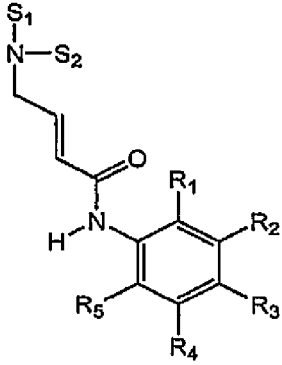

and insert the following structure:

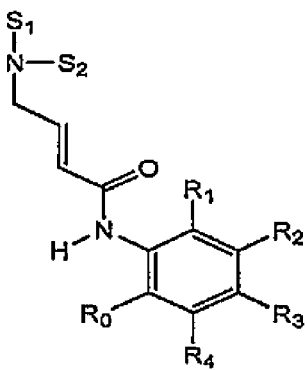

(2) Col. 4, lines 5-14, delete the following structure:

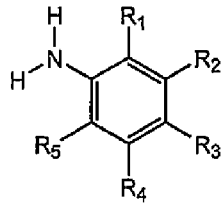

and insert the following structrure:

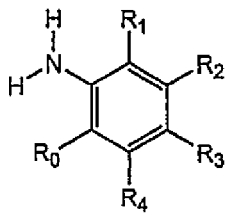

UNITED STATES PATENT AND TRADEMARK OFFICE
CERTIFICATE OF CORRECTION

PATENT NO. : 7,126,025 B2  Page 2 of 4
APPLICATION NO. : 10/758187
DATED : October 24, 2006
INVENTOR(S) : Considine et al.

It is certified that error appears in the above-identified patent and that said Letters Patent is hereby corrected as shown below:

(3)  Col. 4, line 59, replace " "X" " with -- "X'" -- ;

(4)  Col. 6, line 1, replace " R'''SO$_2$NH radical, where R'''' " with
-- R'''SO$_2$NH radical, where R''' -- ;

(5)  Cols. 13-14, lines 15-35, delete the following:

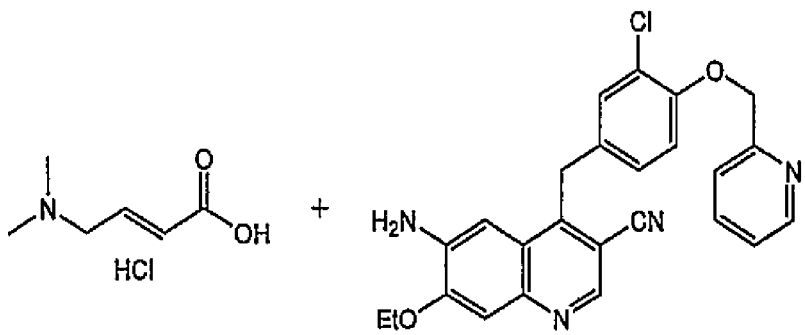

and insert the following:

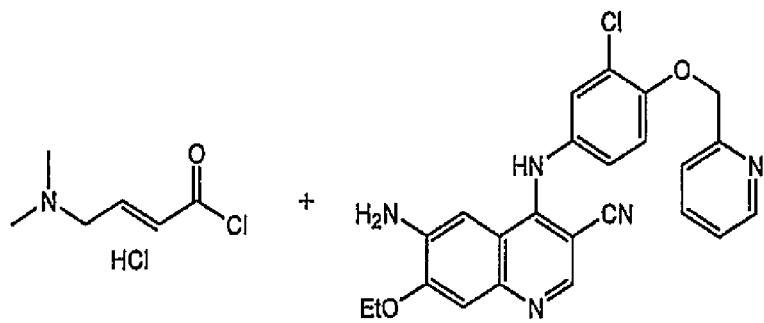

UNITED STATES PATENT AND TRADEMARK OFFICE
CERTIFICATE OF CORRECTION

PATENT NO. : 7,126,025 B2  Page 3 of 4
APPLICATION NO. : 10/758187
DATED : October 24, 2006
INVENTOR(S) : Considine et al.

It is certified that error appears in the above-identified patent and that said Letters Patent is hereby corrected as shown below:

(6) Cols. 15-16, lines 15-35, delete the following structure:

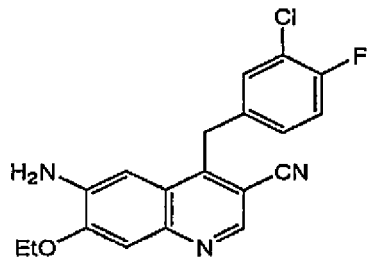

and insert the following structure:

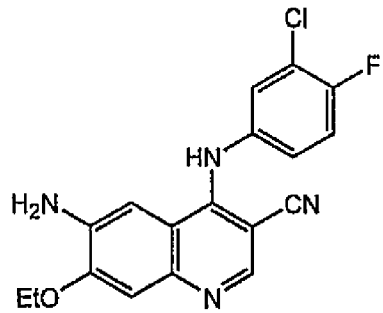

(7) Col. 20, Line 55, delete the second occurrence of "4-Dimethylaminocrotonic acid"

UNITED STATES PATENT AND TRADEMARK OFFICE
CERTIFICATE OF CORRECTION

PATENT NO. : 7,126,025 B2
APPLICATION NO. : 10/758187
DATED : October 24, 2006
INVENTOR(S) : Considine et al.

It is certified that error appears in the above-identified patent and that said Letters Patent is hereby corrected as shown below:

(8)  Claim 5, Col. 23, lines 45-60, delete the following structure:

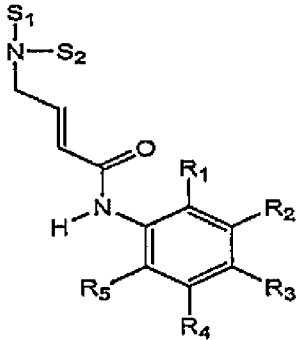

and insert the following structure:

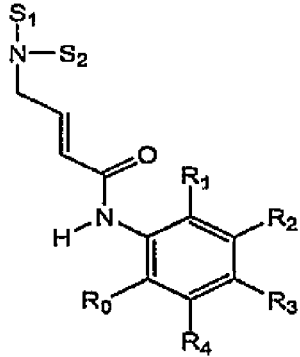

Signed and Sealed this

Fifth Day of June, 2007

JON W. DUDAS
*Director of the United States Patent and Trademark Office*